US00PP36792P2

(12) United States Plant Patent
Saul

(10) Patent No.: US PP36,792 P2
(45) Date of Patent: Jul. 1, 2025

(54) ***STACHYS* PLANT NAMED 'KEY LIME'**

(50) Latin Name: *Stachys byzantina*
Varietal Denomination: KEY LIME

(71) Applicant: Richard Saul, Cleveland, GA (US)

(72) Inventor: Richard Saul, Cleveland, GA (US)

(73) Assignee: Saul Trademarks llc, Cleveland, GA (US)

( * ) Notice: Subject to any disclaimer, the term of this patent is extended or adjusted under 35 U.S.C. 154(b) by 0 days.

(21) Appl. No.: 18/935,710

(22) Filed: Nov. 4, 2024

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Stachys* plant named 'KEY LIME' is disclosed, characterized by bright lime green foliage. Leaves emerge bright lime green and maintain this coloration year-round. Plants are typically 12 to 16 inches in height and spread to around 18 inches. Mature foliage is typically 6 to 8 inches long. The new cultivar is a *Stachys*, suitable for ornamental garden purposes.

3 Drawing Sheets

Figure 1:
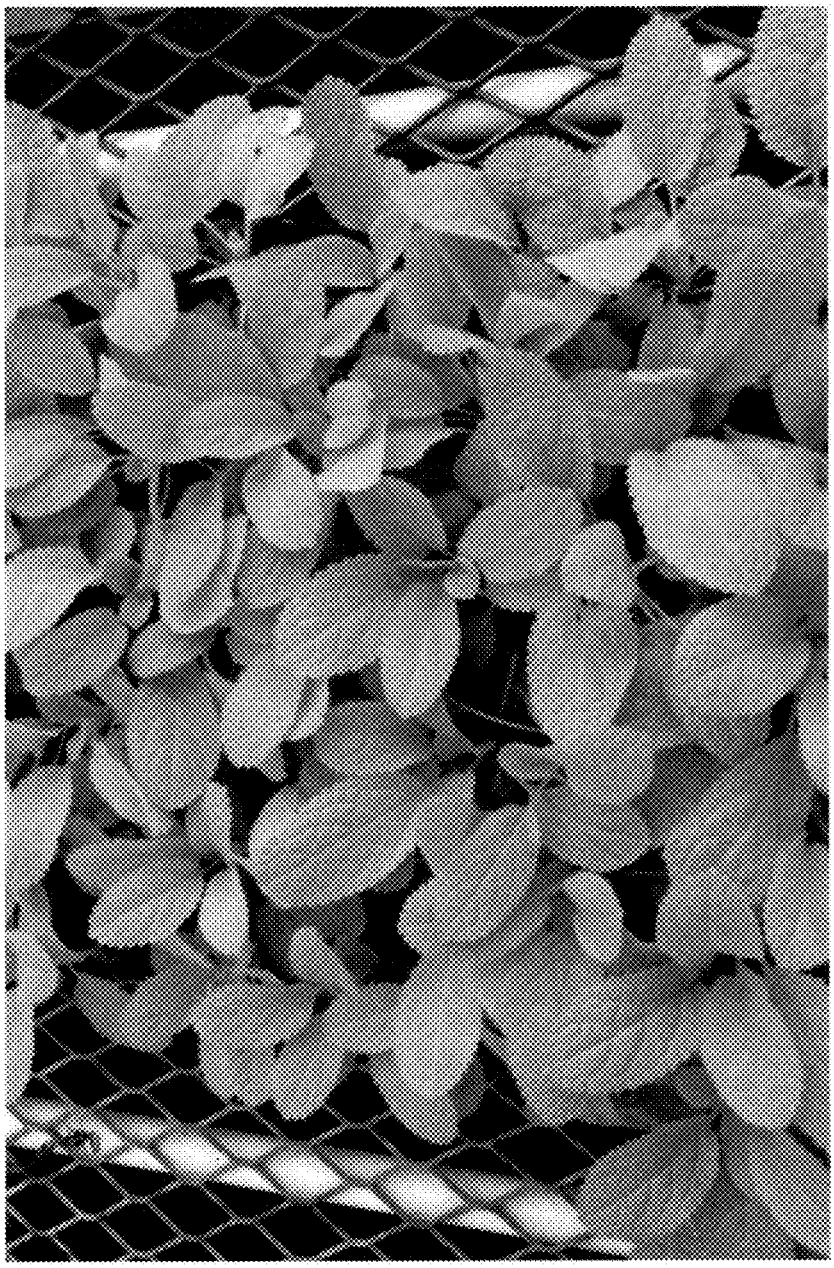

Latin name of the genus and species: *Stachys byzantina.*
Cultivar denomination: 'KEY LIME'.

BACKGROUND OF THE INVENTION

The new cultivar, hereinafter referred to as 'KEY LIME', was discovered at a nursery in Cleveland, GA in a planting of *Stachys byzantina* 'Helen von Stein', unpatented. The interesting new cultivar was discovered as a naturally occurring whole mutation in a planting of the parent variety in March of 2021.

After identifying the new cultivar as a potentially interesting selection, the inventor first asexually propagated 'KEY LIME' in July of 2021, using terminal vegetative cuttings. This took place at the same nursery in Cleveland, GA. The inventor continued controlled testing and propagation, assessing stability of the unique characteristics of this cultivar. At least five generations have been reproduced and have shown that the unique features of this cultivar are stable and reproduced true to type.

SUMMARY OF THE INVENTION

The cultivar 'KEY LIME' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'KEY LIME'. These characteristics in combination distinguish 'KEY LIME' as a new and distinct *Stachys* cultivar:

1. Bright lime green foliage; leaves emerge bright lime green and maintain this coloration year-round.
2. Plants are typically 12 to 16 inches in height and spread to around 18 inches.

4. Mature foliage of 6 to 8 inches long.
5. Reduced blooming compared to the species.

COMPARISON TO PARENT CULTIVAR

'KEY LIME' is similar in most horticultural characteristics to the parent variety. Plants of the new cultivar 'KEY LIME', however, differ in the following:

1. Foliage of the new cultivar is bright lime green; foliage of the parent variety is greyed-green.
2. The parent variety produces more inflorescences than 'KEY LIME'.

COMMERCIAL COMPARISON

'KEY LIME' is similar in most horticultural characteristics to the unpatented commercial cultivar *Stachys byzantina* 'Primrose Heron'. Plants of the new cultivar 'KEY LIME', however, differ in the following:

1. Foliage of the new cultivar emerges bright lime green and maintains this color year round; foliage of this comparator emerges pale green and turn greyed-green in the Summer.
2. Plants of the new cultivar are typically 12 to 16 inches in height; plants of this comparator are typically 4 to 6 inches in height.
3. Plants of the new cultivar are typically 18 inches in diameter; plants of this comparator are typically 18 to 30 inches in diameter.
4. Foliage of the new cultivar are typically 6 to 8 inches long; foliage of this comparator is typically 4 inches long.

BRIEF DESCRIPTION OF THE PHOTOGRAPHS

The accompanying photograph in FIG. 1 illustrates in full color typical young plants of 'KEY LIME' grown in a propagation tray in Cleveland, GA. The plants are approximately about 6 weeks old.

Figure 2:
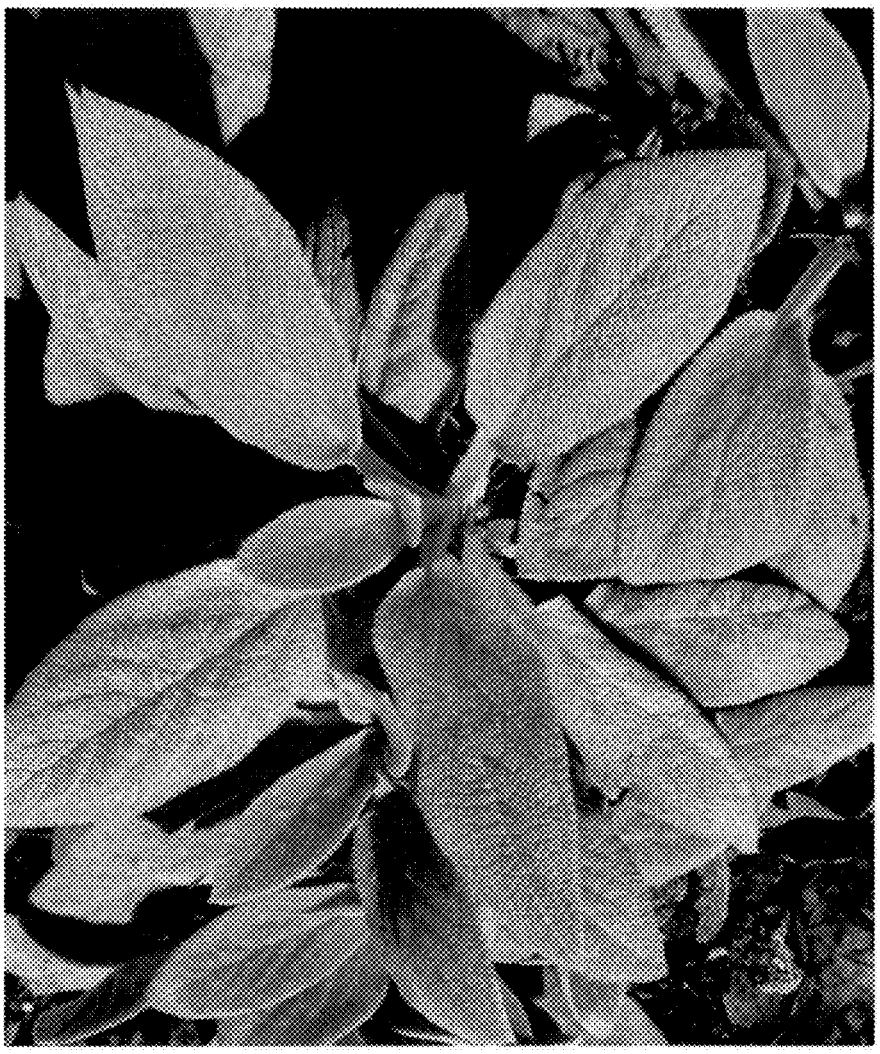

FIG. 2. is a plant of about 6 months old, grown outdoors in Camarillo, CA, photographed during late Summer.

Figure 3:
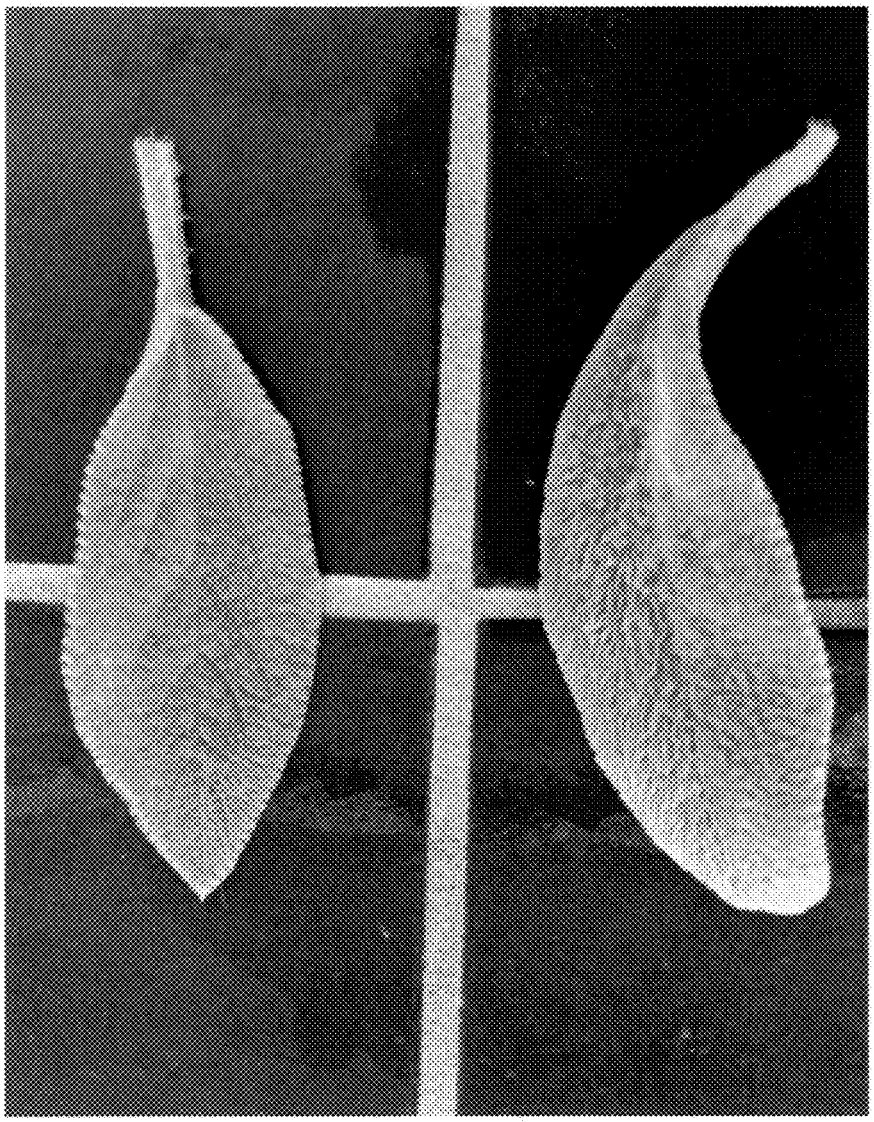

FIG. 3 is a comparison of foliage of the parent variety (bottom leaf) and 'KEY LIME' (top leaf). Photographed during late Summer.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'KEY LIME' plants grown outdoors in Camarillo, CA in a one-gallon pot. Plants are approximately 6 months old and described during August and September. Measurements and numerical values represent averages of typical plant types.

Botanical classification: *Stachys byzantina* 'KEY LIME'.

ROOTS

Root description: Fine, densely fibrous. Colors include Orange-White 159B on new growth; Grey-Brown N199A for older roots.

Stolons: 5 to 9 mm in diameter. Stolon diameter about 3 to 7 mm. Stolon length 8 to 24 cm. Colored Grey-Brown N199A.

Time to initiate roots: 5 to 7 days at approximately 25° C.

Time to produce a rooted cutting: 10 to 14 days at 25° C.

PLANT

Pot size of plant described: 1-gallon pot

Growth habit: Semi upright and creeping flowering perennial. Branches are semi-upright, creeping growth by stolons.

Height: Approximately 30 to 40 cm.

Plant spread: Approximately 35 to 40 cm.

Growth rate: Rapid.

Branching characteristics: Abundant basal branching. Creeping and rooting easily.

Quantity of branches: 15 to 25.

Length of branches: Approximately 2 to 5 cm.

Diameter of branches: Approximately 1 cm.

*Color*.—Near RHS Green 138A.

*Texture*.—Pubescent and ribbed.

Internode: Internode from stolon 1.5 to 4 cm. No branch internodes.

Age of plant described: Approximately 6 months from 1 rooted cutting.

FOLIAGE

Leaf:

*Arrangement*.—Rosette.

*Quantity*.—40 to 50 on a mature plant.

*Average Length*.—15 to 20 cm. including petiole.

*Average Width*.—6 to 8 cm.

*Shape of blade*.—Somewhat narrow ovate.

*Aspect*.—Slight upward fold.

*Foliage fragrance*.—Faint, earthy scent.

*Apex*.—Acute.

*Base*.—Truncate.

*Attachment*.—Stalked.

*Margin*.—Very finely dentate. Ciliate.

*Texture of top surface*.—Densely pubescent, soft.

*Texture of bottom surface*.—Short, dense pubescence. Longer, pubescence along veins. Reticulate.

*Color*.—Young foliage upper side: Near RHS Yellow-Green 145C flushed 150B. Young foliage under side: Near RHS Yellow-Green 145C. Mature foliage upper side: Near RHS Yellow-Green 145C flushed 150B. Mature foliage under side: Near Yellow-Green 145C.

*Venation*.—Type: Reticulate. Venation color upper side: Near RHS Yellow-Green 149D. Venation color under side: Near RHS Yellow-Green 145D.

*Petiole*.—Average Length: Approximately 3.5 cm. Diameter: Approximately 5 to 6 mm. Texture: Dense, soft pubescence. Color: Near RHS Yellow-Green 149D flushed 150D.

FLOWER

Natural flowering season: Flowering from early Summer until mid-Fall.

Inflorescence type and habit: Flowers arranged in verticillasters on spikes.

Flower longevity on plant: Individual flowers last approximately 10 to 14 days on the plant. Each spike lasts approximately 4 to 6 weeks with flowers. Corolla self-cleaning, calyx persistent.

Quantity of flowers: About 40 to 60 flowers per spike. Mature plants have approximately 2 to 5 spikes.

Spike size:

*Diameter*.—Approximately 3 cm.

*Height*.—15 to 25 cm.

*Inflorescence internode*.—15-20 mm.

*Number of florets per node*.—8 to 10 per node.

Individual flowers:

Size:

*Diameter*.—Approximately 1 cm.

*Length*.—Approximately 1.5 cm.

*Fragrance*.—Moderate herbaceous scent.

Corolla:

*Petal arrangement*.—The corolla is sympetalous and typically bilabiate with 2 small, fully fused lobes forming a single upper lip and 3 larger fused lobes forming a lower lip

*Margin*.—Entire.

*Tip shape*.—Upper lip tip obtuse, lower lip tip retuse.

*Length*.—Upper lip Approximately 5 mm. Lower lip Approximately 9 mm. Tube length Approximately 6 mm.

*Width*.—Upper lip: Approximately 4 mm, lower lip Approximately 5 mm. Tube width: Approximately 5 mm.

*Texture*.—Upper lip: Glabrous all surfaces. Lower lip: Glabrous all surfaces.

*Corolla tube*.—Length: 4 mm. Diameter: 3 mm. Texture: Glabrous.

Color: Upper lip:

*When opening*.—Inner surface: Near RHS Red-Purple N64A. Outer surface: Near RHS Red-Purple N72B.

*Fully opened*.—Inner surface: Near RHS Red-Purple 72A. Outer surface: Near RHS Red-Purple N72B.

*Fading*.—Inner surface: Near RHS Purple 77A. Outer surface: Near RHS Purple N78D.

Color: Lower lip:

*When opening*.—Inner surface: Near RHS Red-Purple N64A. Outer surface: Near RHS Red-Purple N72B.

*Fully opened*.—Inner surface: Near RHS Red-Purple 72A. Outer surface: Near RHS Red-Purple N72B.

*Fading*.—Inner surface: Near RHS Purple 77A. Outer surface: Near RHS Purple N78D.

Color: Tube:

*When opening*.—Inner surface: Near RHS Purple 76D. Outer surface: Near RHS Purple 76C.

*Fully opened*.—

*Opening*.—Inner surface: Near RHS Purple 76C. Outer surface: Near RHS Purple 76B.

Bud: Flower bud includes immature calyx which completely surrounds immature corolla.

*Shape*.—Ovoid.

*Length*.—Approximately 1.0 cm.

*Diameter*.—Approximately 6 mm.

*Texture*.—Softly pubescent.

*Color*.—Near RHS Greyed-Green 192B.

Calyx:

*Length*.—Approximately 1 cm.

*Diameter*.—Approximately 6 mm.

*Shape*.—Tubular, weakly flared distally.

Sepals:

*Shape*.—Quantity per flower: 5, fused to form a tube. Unfused apex.

*Length*.—Approximately 3 mm unfused portion.

*Width*.—Approximately 5 mm.

*Margin*.—Entire.

*Apex*.—Acute.

*Texture*.—Densely, long, soft pubescence.

*Color*.—Near RHS Greyed-Green 190C.

Peduncle:

*Length*.—Average 3.0 cm.

*Diameter*.—6 mm.

*Color*.—Greyed-Green 190C.

*Orientation*.—Straight, approximately 15-degree angle from center of plant.

*Strength*.—Strong.

*Texture*.—Densely, long, soft pubescence.

Pedicels: Not present.

REPRODUCTIVE ORGANS

Stamens:

*Number*.—2 to 6.

*Filament length*.—Unfused section 3 to 75 mm.

*Filament color*.—Near RHS Red-Purple N74C.

Anthers:

*Shape*.—Linear.

*Length*.—1 mm.

*Color*.—Near RHS Red-Purple 60C.

*Pollen*.—Scant pollen observed, colored near RHS Yellow-White 158C.

Pistil:

*Number*.—1.

*Length*.—1.2 cm.

*Style*.—Length: 1 cm. Color: Near RHS White N155C at base, distally turning Purple 75C.

*Stigma*.—Shape: Forked. Color: Near RHS Purple 77A. Ovary: Colored near RHS Yellow-Green 150D, round, approximately 2 mm in diameter.

OTHER CHARACTERISTICS

Seeds: 1 to 4 seeds per pod, approximately 2 mm long and 2 mm wide. Slightly irregular orbicular. Colored near Brown 200B.

Disease/pest resistance: Neither resistance nor susceptibility to normal diseases and pests of *Stachys byzantina* has been observed.

Drought tolerance: Observed to tolerate drought when planted in the ground.

Temperature tolerance: USDA zones 4 to 8.

What is claimed is:

1. A new and distinct cultivar of *Stachys* plant named 'KEY LIME' as herein illustrated and described.

* * * * *